United States Patent [19]

Patchornik et al.

[11] 3,919,206

[45] Nov. 11, 1975

[54] 7-(HALOMETHYLARYL)-ACETAMIDOCEPHALOSPORIN DERIVATIVES

[75] Inventors: Abraham Patchornik, Ness-Ziona; Fortuna Haviv, Rehovot, both of Israel

[73] Assignee: Yeda Research and Development Company, Ltd., Rehovot, Israel

[22] Filed: Sept. 25, 1973

[21] Appl. No.: 400,560

[52] U.S. Cl.................. 260/243 C; 260/332.2 A; 260/515 M; 260/516; 260/518 A; 260/519; 260/520; 260/521 A; 424/246

[51] Int. Cl.$^2$ .............. C07D 501/28; C07D 501/34; A61K 31/545

[58] Field of Search ................... 260/243 C

[56] References Cited
UNITED STATES PATENTS

| | | | |
|---|---|---|---|
| 3,487,074 | 12/1969 | Sheehan | 260/243 C |
| 3,814,754 | 6/1974 | Jackson | 260/243 C |

Primary Examiner—R. Gallagher
Assistant Examiner—Diana G. Rivers
Attorney, Agent, or Firm—L. Ruth Hattan; Eugene O. Retter; George W. Rauchfuss, Jr.

[57] ABSTRACT

Novel 7-(halomethylaryl)acetamidocephalosporin derivatives useful as antibiotic agents.

17 Claims, No Drawings

7-(HALOMETHYLARYL)ACETAMIDOCEPHALOSPORIN DERIVATIVES

FIELD OF THE INVENTION

This invention relates to novel cephalosporin derivatives useful as antibiotics and processes for their preparation.

DESCRIPTION OF THE PRIOR ART

Netherlands application Ser. No. 6916151 published Apr. 29, 1971, describes compounds of the following general formula wherein the substituents as represented by $R^2$ and $R^3$ may optionally be substituted with a haloalkyl group:

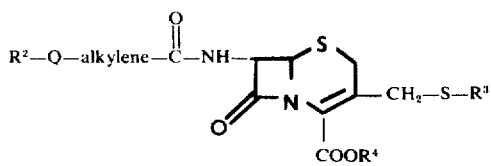

wherein $R^2$ represents optionally substituted thienyl, diazolyl, triazolyl, tetrazolyl, thiazolyl, thiadiazolyl, thiatriazolyl, oxazolyl, oxadiazolyl, pyridyl, diazinyl, benzothiazolyl, benzimidazolyl, benzoxazolyl, and benzotriazolyl; $R^3$ represents optionally substituted diazolyl, triazolyl, tetrazolyl, thiazolyl, thiadiazolyl, thiatriazolyl, oxazolyl, oxadiazolyl, benzimidazolyl, benzoxazolyl, triazolopyridyl, diazinyl and purinyl; $R^4$ represents hydrogen or an alcohol residue; and Q represents a bond or sulfur.

All of the compounds in the above described Netherlands Application are substituted at the 3-position of the cephalosporin ring with a methylenethio substituent. This application does not describe or suggest the compounds of the instant invention.

SUMMARY OF THE INVENTION

Compounds of the following general Formula I are useful as antibiotic agents:

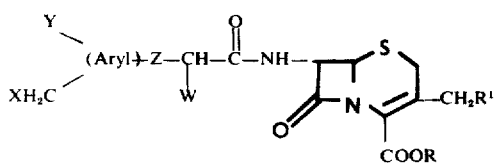

wherein Aryl represents phenyl or 2-thienyl; X is selected from chlorine, bromine or fluorine; Y is selected from hydrogen, chlorine, bromine, straight or branched lower alkyl of from 1 to 4 carbon atoms, lower alkoxy of from 1 to 4 carbon atoms and -$CH_2X$ wherein X represents bromine, chlorine or fluorine with the proviso that when Aryl represents 2-thienyl, Y is hydrogen, Z represents a bond, oxygen or sulfur with the proviso that when Aryl is 2-thienyl, Z is a bond; W represents hydrogen, methyl, $NH_2$, OH, —COOH or —$SO_3H$ with the proviso that when Z is oxygen or sulfur, W is other than OH; R represents hydrogen or a pharmaceutically acceptable non-toxic cation or an anion charge; and $R^1$ represents hydrogen or acetoxy.

The non-toxic acid addition salts of the compounds wherein W represents $NH_2$, such as mineral acid addition salts, for example, hydrogen chloride, hydrogen bromide, hydrogen iodide, sulfate, sulfamate and phosphate and organic acid addition salts, for example, maleate, acetate, citrate, oxalate, succinate, benzoate, tartrate, fumarate, malate, mandelate and ascorbate, are also included within the scope of this invention.

Also within the scope of this invention are the non-toxic pharmaceutically acceptable salts of the compounds of general Formula I wherein W represents COOH or $SO_3H$ and compounds wherein R represents hydrogen. Illustrative pharmaceutically acceptable salts of these acid derivatives are primary, secondary of tertiary amines, for example, cyclohexylamine, ethylamine and pyridine.

The pharmaceutically acceptable cations which may be present as the group R in the compounds of general Formula I include alkali metal ions, for example sodium ion, potassium ion, calcium ion as well as ammonium, and organic amine cations, for example, lower alkyl ammonium groups, such as triethylammonium, and N-ethylpiperidine.

DETAILED DESCRIPTION OF INVENTION

Illustrative of straight or branched lower alkyl groups which Y may represent in compounds of the above general Formula 1 are methyl, ethyl, n-propyl, isopropyl, n-butyl, and tert-butyl.

Illustrative examples of lower alkoxy groups which Y may represent in compounds of general Formula 1 are methoxy, ethoxy, propoxy and butoxy.

When the Aryl group in the compounds of general Formula 1 represents phenyl, each of the substitutents —$CH_2X$ and Y may be individually attached to any of the positions 2 through 6 of the phenyl ring. The preferred positions of attachment of the —$CH_2$—X group are the ortho- and parapositions of the phenyl group.

When the aryl group in the compounds of general Formula I represents thienyl, it is attached to the $$-\underset{W}{\underset{|}{CH}}-$$

moiety at the 2-position of the thienyl group. The substituent as represented by —$CH_2$—X is attached at the 4 or 5 position of the thienyl group.

It is apparent from the foregoing description that the compounds of this invention are halomethylated phenyl substituted cephalosporin derivatives as represented by the following general Formula II,

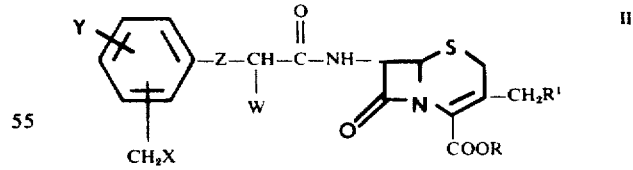

or are halomethylated thienyl substituted cephalosporin derivatives as represented by the following general Formula III.

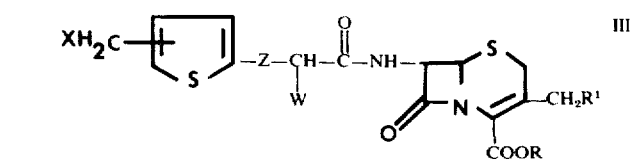

In the above general Formulas II and III, the various substituent groups as represented by Y, CH₂X, Z, W, R and R¹ have the meanings as defined in general Formula I.

The compounds of general Formula I are prepared by coupling 7-aminocephalosporanic acid or a derivative thereof having the formula

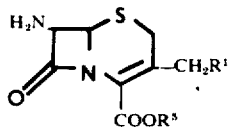

wherein R⁵ is hydrogen or a pharmaceutically acceptable nontoxic cation, and R¹ has the meanings defined in general Formula I with an acid of the following Formula V or a functional equivalent thereof

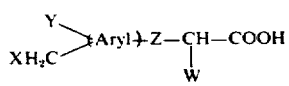

wherein Aryl, Y, CH₂X, Z and W have the meanings defined in general Formula I. When the substituent group W in the above formula V represents an amino group suitable blocking groups, for example, tert-butoxycarbonyl, or carbobenzyloxy are employed to protect the amino function. Such blocking groups are removed after the coupling reaction by methods generally known in the art, for example, as described by Lemieux et al., in U.S. Pat. No. 3,657,232.

Functional equivalents of the acids as represented by Formula V include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester or thioester, for example, with p-nitrophenol, 2,4-dinitrophenol, or thioacetic acid, may be used, or the free acid as represented by Formula V may be coupled with the 7-aminocephalosporanic acid derivative as represented by Formula IV after first reacting the acid with N,N'-dimethylchoroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide.

The coupling reaction is generally carried out in the presence of a solvent. Suitable solvents include ethyl acetate, acetone, dioxane, acetonitrile, chloroform, ethylene chloride, tetrahydrofuran and dimethylformamide. As hydrophilic solvents are employed mixtures of these solvents with water are also suitable for the above reaction. The coupling reaction is generally carried out in the presence of a base, for example, an alkaline bicarbonate. The temperature of the reaction may vary from −10° to 100°C, and the reaction time may vary from about ½ hour to 10 hours. The cephalosporin products are isolated by conventional methods.

The compounds of general Formula I may also be prepared by combining a modified polystyrene containing nitrophenol or hydroxysuccinimide groups with an acid of general Formula V and mixing the activated acid thus formed with a compound of general Formula IV by the general procedure described in Canadian Pat. No. 892,580, issued Feb. 8, 1972, by substituting a compound of general Formula IV for the penicillanic acid derivatives described therein.

The salt forms of Formula I wherein R is a pharmaceutically acceptable cation are prepared in the manner recognized in the art and may be formed in situ or by reacting the corresponding acid with base for example sodium bicarbonate or triethylamine.

The individual optical isomers of the compounds of general Formula I wherein W represents methyl, NH₂, OH, COOH or SO₃H are also included within the scope of this invention.

The compounds of general formula IV, that is, 7-aminocephalosporanic acid and 7-aminodesacetoxycephalosporanic acid and salts thereof are commercially available or may be obtained from Cephalosporin C by procedures well known in the art.

The halomethylated aromatic acids as represented by general Formula V are prepared by direct halomethylation of the acid as represented by the following Formula VI:

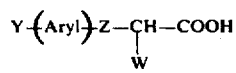

wherein Aryl, Y, Z and W have the meanings defined in general Formula I. When the substituent group W in compounds of Formula VI represents amino, the amino group is protected by a suitable blocking group, for example an acyl group, such as, acetyl or trifluoroacetyl, prior to the halomethylation reaction. Upon completion of the halomethylation reaction the blocking group may be removed by acid hydrolysis by procedures known in the art.

The halomethylated derivatives of the compounds of Formula VI are obtained by several methods. For example, by the reaction of a compound of Formula VI with paraformaldehyde in the presence of a Lewis acid, such as, ZnCl₂, AlCl₃, SnCl₄, or ClSO₃H in a solvent, such as, petroleum ether, chloroform, carbontetrachloride, or benzene at a temperature ranging from −10° to 100°C during which time hydrogen chloride gas or hydrogen bromide gas is bubbled into the reaction mixture, compounds of the general Formula V are obtained.

The reaction of an acid of Formula VI with 38-38% formalin in concentrated hydrochloric acid at temperatures ranging from −10° to 100°C during which time hydrogen chloride gas or hydrogen bromide gas is bubbled through the reaction mixture also yields compounds of general Formula V.

Additionally upon reaction of an acid of Formula VI with trioxane in acetic acid or phosphoric acid at temperatures of from −10° to 100°C during which time hydrogen bromide or hydrogen chloride gas in bubbled through the reaction mixture, compounds of general Formula V are obtained. Or, the reaction of an acid of Formula VI in the presence of a Lewis acid, such as those described hereinabove, with chloromethylether at temperatures from −10° to 100°C, or the reaction of the acid in acetic acid or concentrated sulfuric acid with dichloromethyl ether in the presence of zinc chloride will give compounds of general Formula V.

The compounds of Formula V wherein W represents COOH, and Aryl is phenyl are preferably obtained by treating the corresponding diethyl ester of Formula VI with 40% formalin in the presence of anhydrous zinc chloride in benzene at about 50°C during which time hydrogen chloride or hydrogen bromide gas is bubbled into the reaction mixture followed by acid hydrolysis.

Compounds of Formula V wherein W represents SO₃H may be obtained by the halomethylation reactions described above using an acid of Formula VI wherein W represents SO₃H or the methyl ester thereof in which latter case the resulting chloromethylated compound is converted to the free SO₃H acid by acid hydrolysis.

In the halomethylation of compounds of Formula VI wherein W represents OH it may be advantageous to protect the OH group prior to halomethylation as described by B. Reichert, et al., Pharmazie 5, 10 (1950).

The compounds as represented by Formula VI are readily available or may be prepared by generally known methods.

The novel compounds of this invention are useful as antibiotic agents as demonstrated by their activity against gram positive and gram negative bacteria in vitro and in vivo and fungi. The compounds of this invention are particularly useful in that they possess a longer duration of activity than many of the well known cephalosporin compounds. Also, as is well known in the art, cephalosporin compounds generally have an unpleasant taste. The compounds described herein possess a markedly improved taste.

The compounds of this invention may be administered in a manner similar to that of many well known cephalosporin compounds, for example, cephalexin, cephalothin, or cephaloglycine. They may be administered alone or in the form of pharmaceutical preparations either orally, parenterally and topically to warm blooded animals, that is, birds and mammals, for example, felines, canines, bovines, and equines, and humans. For oral administration the compounds may be administered in the form of tablets, capsules or pills or in the form of elixirs or suspensions. For parenteral administration they are best used in the form of a sterile aqueous solution which may contain other solutes, for example, enough saline or gluose to make the solution isotonic. For topical administration the compounds may be incorporated into creams or ointments.

Illustrative examples of bacteria against which the compounds of this invention are active are *Staphylococcus aureus*, *Salmonella schottmuelleri*, *Klebsiella pnumoniae*, *Diplococcus pneumonia*, and *Streptococcus pyogenes*.

The compounds of this invention as described by general Formula II are halomethylated phenylacetamido-, halo-methylated phenoxyacetamido-, and halomethylated phenylthioacetamido cephalosporin derivatives wherein the phenyl ring may be further substituted with straight or branched alkyl containing from 1 to 4 carbon atoms, alkoxy containing from 1 to 4 carbon atoms, chlorine, bromine or —CH₂X wherein X is chlorine, bromine or fluorine. When Y represents hydrogen in the compounds of general Formula II, the phenyl ring could also be substituted with hydroxy or trifluoromethyl.

The compounds of this invention as represented by general Formula III are halomethylated 2-thienylacetamido cephalosporin derivatives. Compounds of general Formula III could also be further substituted on the thienyl ring with the substituents as represented by Y in compounds of general Formula II.

A preferred group of compounds of this invention are represented by the following Formula VII:

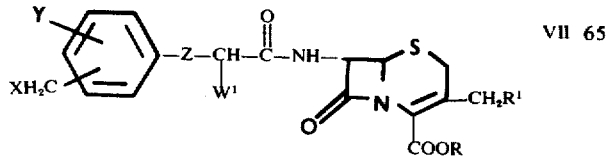

wherein W¹ represents hydrogen, methyl, amino or hydroxy; and X, Y, Z, R and R¹ have the meanings defined in general Formula I.

A more preferred group of compounds of this invention are those of general Formula VII wherein Y represents hydrogen or alkoxy of from 1 to 4 carbon atoms; and X, W¹, R and R¹ have the meanings defined in general Formula VII.

A still more preferred group of compounds of this invention are those of general Formula VII wherein Y represents hydrogen, alkoxy of from 1 to 4 carbon atoms; Z represents a bond; and X, W¹, R and R¹ have the meanings defined in general Formula VII.

Another preferred group of compounds of this invention are represented by the following Formula VIII:

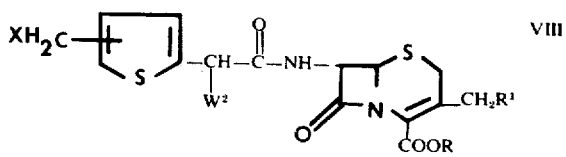

wherein W² represents hydrogen or methyl; and X, R and R¹ have the meanings defined in general Formula I.

The following examples are illustrative of the invention.

EXAMPLE 1 p-Chloromethylphenylacetyl chloride

A. At a temperature of from −10° to 0°C hydrogen chloride gas is bubbled through a stirred mixture of 102 g of phenylacetic acid, 67.5 g of paraformaldehyde and 67.5 g of zinc chloride in 1000 ml of petroleum ether for 1 hour. Stirring is continued for about 1 hour at room temperature after which the mixture is refluxed for about 2 hours during which time hydrogen chloride gas is bubbled into the mixture. To the reaction mixture is added 1000 ml each of methylene chloride and water. The organic phase is separated and the aqueous phase is extracted twice with methylene chloride. The combined organic phases are combined and extracted four times with a saturated sodium bicarbonate solution. The organic neutral phase is dried over anhydrous sodium sulfate, filtered and the solvent is removed under vacuum to give a neutral by-product which is further identified in Example 4 below. The basis aqueous phase is separated and acidified with cold concentrated hydrochloric acid to pH 2–3, then extracted three times with methylene chloride. The methylene chloride fraction is dried over anhydrous sodium sulfate, filtered and the sovlent evaporated. The resulting oily acidic product is chromatographed on silica gel using benzene and benzeneacetone as the eluant to give p-chloromethylphenylacetic acid which is recrystallized from hot chloroform. M.P. 147°–149°C.

B. A mixture of 1 g of p-chloromethylphenylacetic acid and 6 ml of thionyl chloride is stirred at room temperature for 25 hours after which the excess thionyl chloride is removed under vacuum to yield p-chloromethylphenylacetyl chloride. M.P. 35°–50°C.

EXAMPLE 2

3-[(Acetyloxy)methyl]-7-[[2-[4-(chloromethyl)-phenyl]-acetyl]amino]-8-oxo-5-thia-1-azabicyclo[4.2.0.]oct-2-ene-2-carboxylic acid A mixture of 1 g of 7-aminocephalosporanic acid and 1 g of p-chloromethylphenylacetyl chloride in 45 ml of ethyl acetate is refluxed for about 2 hours after which the solvent is removed under vacuum yielding a yellow-brown amorphous product which is chromatographed on silica gel using benzene-acetone as the eluant to give 3-[(acetyloxy)methyl]-7-[[2-[4-(chloromethyl)-phenyl]acetyl]amino]-8-oxo-5-thia-1-azabicyclo[4.2.0.]oct-2-ene-2-carboxylic acid. M.P. 164°–165°C (dec.).

EXAMPLE 3

7-[[-2-[4-(Chloromethyl)phenyl]acetyl]amino]-3-methyl-8-oxo-5-thia-1-azabicyclo[4.2.0.]oct-2-ene-2-carboxylic acid By the procedure of Example 2, only substituting 1 g of 7-aminodesacetoxycephalosporanic acid for 7-aminocephalosporanic, 7-[[-2-[4-(chloromethyl)-phenyl]acetyl]amino]-3-methyl-8-oxo-5-thia-1-azabicyclo[4.2.0.]oct-2-ene-2-carboxylic acid is obtained. M.P. 145°–146°C.

EXAMPLE 4 o-Hydroxymethylphenylacetic acid lactone

The neutral by-product obtained in Example 1 is purified by sublimation under vacuum (0.05 mm Hg at 80°C) to give o-hydroxymethylphenylacetic acid lactone. M.P. 82°C.

EXAMPLE 5 o-Bromomethylphenylacetyl chloride

To a solution of 5 ml of glacial acetic acid saturated with hydrogen bromide gas is added at 0°C a solution of o-hydroxymethylphenylacetic acid lactone (0.55 g) in 2 ml of glacial acetic acid. The mixture is stirred at room temperature for 2 hours then refluxed for 1 hour during which time hydrogen bromide gas is bubbled into the mixture. The excess lactone and solvent are removed under high vacuum at room temperature. The resulting oily residue is triturated three times with hexane to give o-bromomethylphenylacetic acid. M.P. 110°C.

A solution of 0.18 g of o-bromomethylphenylacetic acid in excess thionyl chloride is stirred at room temperature for 18 hours after which the unreacted thionyl chloride is removed under high vacuum to give o-bromomethylphenylacetyl chloride as an oily residue.

EXAMPLE 6

7-[[-2-[2-(Bromomethyl)phenyl]acetyl]amino]-3-methyl-8-oxo-5-thia-1-azabicyclo[4.2.0.]oct-2-ene-2-carboxylic acid A mixture of 0.175 g of o-bromomethylphenylacetyl chloride and 0.175 g of 7-aminodeacetoxycephalosporanic acid in 40 ml of ethyl acetate is refluxed for 50 minutes after which the solvent is removed under vacuum yielding an oily residue which is chromatographed on silica gel using benzene and benzene-acetone as the eluant to give 7-[[-2-[2-(bromomethyl)phenyl]acetyl]amino]-3-methyl-8-oxo-5-thia-1-azabicyclo[4.2.0-.]oct-2-ene-2-carboxylic acid. M.P. 145°C (dec.).

EXAMPLE 7

3-[(Acetyloxy)methyl]-7-[[2-[2-(bromomethyl)-phenyl]acetyl]-amino]-8-oxo-5-thia-1-azabicyclo[4.2.0.]oct-2-ene-2-carboxylic acid When in the procedure of Example 6, 0.175 g of 7-aminocephalosporanic acid is substituted for 7-aminodesacetoxycephalosporanic acid is substituted for 7-aminodesacetoxycephalosporanic acid, 3-[(acetyloxy)methyl]-7-[[2-[2-(bromomethyl)phenyl]acetyl]amino]-8-oxo-5-thia-1-azabicyclo-[4.2.0.]oct-2-ene-2-carboxylic acid is obtained.

EXAMPLE 8 o-Chloromethyl-p-methoxymandelic acid chloride

A solution of 1.1 g of 2-chloromethyl-4-methoxymandelic acid, obtained by the procedure described by B. Reichert et al., Pharmazie 5, 10 (1950), in 25 ml of thionyl chloride is stirred at room temperature for about 16 hours after which the excess thionyl chloride is removed under high vacuum to give o-chloromethyl-p-methoxymandelic acid chloride as an oil.

EXAMPLE 9

3-[(Acetyloxy)methyl]-7-[[2-[2-(chloromethyl)-4-methoxyphenyl]-2-hydroxyacetyl]amino]-8-oxo-5-thia-1-azabicyclo-[4.2.0.]oct-2-ene-2-carboxylic acid.

A mixture of 1 g of 7-aminocephalosporanic acid and 1.2 g of 2-chloromethyl-4-methoxymandelic acid chloride in 200 ml of ethyl acetate is refluxed for 50 minutes after which the solvent is removed under high vacuum. The resulting product is chromatographed on silica gel using benzene-acetone as the eluant. The product obtained is triturated with ether to give 3-[(acetyloxy)methyl]-7-[[2-[2-chloromethyl)-4-methoxyphenyl]-2-hydroxyacetyl]amino]-8-oxo-5-thia-1-azabicyclo[4.2.0.]oct-2-ene-2-carboxylic acid. M.P. 140°–142°C (dec.).

EXAMPLE 10

7-[[2-[2-(Chloromethyl)-4-methoxyphenyl]-2-hydroxyacetyl]-amino]-3-methyl-8-oxo-5-thia-1-azabicyclo[4.2.0.]oct-2-ene-2-carboxylic acid When in the procedure of Example 9, 1 g of 7-aminodesacetoxycephalosporanic acid is substituted for 7-aminocephalosporanic acid, 7-[[2-[2-(chloromethyl)-4-methoxyphenyl]-2-hydroxyacetyl]amino]-3-methyl-8-oxo-5-thia-1-azabicyclo[4.2.0.]oct-2-ene-2-carboxylic acid is obtained.

EXAMPLE 11

2,4-Bis(chloromethyl)phenoxyacetyl chloride

A. Into a mixture of 18 g of phenoxyacetic acid, 80 ml of 36–38% formalin and 100 ml of concentrated hydrochloric acid is bubbled hydrogen chloride gas for 1 hour at room temperature and for 10 minutes at 75°C. The temperature of the mixture is maintained at 75°C. for 1½ hours. To the reaction mixture 1000 ml of methylene chloride and 150 ml of water are added, and the mixture is agitated. The organic phase is separated, dried over anhydrous sodium sulfate, filtered and concentrated to an oily residue under vacuum at 35°C. The oily residue is chromatographed on silica gel using benzene and benzene-acetone as the eluant to give 2,4-bis(chloromethyl)phenoxyacetic acid which is recrystallized from chloroform-hexane. M.P. 110°–111°C.

B. A solution of 2 g of 2,4-bis(chloromethyl)phenoxyacetic acid in 15 ml of thionyl chloride is stirred at room temperature for about 16 hours after which the excess thionyl chloride is removed under high vacuum at room temperature to give 2,4-bis(chloromethyl)-phenoxyacetyl chloride as a semisolid.

EXAMPLE 12

3-[(Acetyloxy)methyl]-7-[[2-[2,4-bis(chloromethyl)]-phenoxy]-acetyl]amino]-8-oxo-5-thia-1-azabicyclo[4.2.0]oct-2-ene-2-carboxylic acid A mixture of 0.25 g of 2,4-bis(chloromethyl)phenoxyacetyl chloride and 0.25 g of 7-aminocephalosporanic acid in 150 ml of ethyl acetate is refluxed for 50 minutes after which the solvent is removed under high vacuum leaving an oily product which is triturated with ether. The resulting product is chromatographed on silica gel using benzene and benzene-acetone as the eluant to give 3-[(acetyloxy)methyl]-7-[[2-[2,4-bis(-chloromethyl)]phenoxy]acetyl]amino]-8-oxo-5-thia-1-azabicyclo[4.2.0.]oct-2-ene-2-carboxylic acid. M.P. 137°–138°C.

EXAMPLE 13

5-Chloromethyl-2-thienylacetyl chloride

2-Thiophenecarboxylic acid is treated in a solution of chloroform with chloromethyl ether in the presnce of 0.9 to 2.2 equivalents of aluminum chloride to give 5-chloromethyl-2-thienylcarboxylic acid. Treatment of the obtained acid with excess thionyl chloride at room temperature for about 16 hours yields the acid chloride which is reacted with diazomethane to give the corresponding diazoketone. A methanol solution of the diazoketone is irradiated under nitrogen for about one hour with a high pressure mercury lamp using a Quarz filter. The methyl 5-chloromethyl-2-thienylacetate is obtained upon work up and column chromatography on silica gel. The acetate is hydrolyzed by treatment of a 1:1 mixture of acetic acid and concentrated hydrochloric acid at room temperature overnight to give 5-chloromethyl-2-thienylacetic acid.

When in the procedure of Example 1 B 5-chloromethyl-2-thienylacetic acid is substituted for p-chloromethylphenyl acetic acid, 5-chloromethyl-2-thienylacetyl chloride is obtained.

EXAMPLE 14

3-[(Acetyloxy)methyl]-7-[[2-[5-(chloromethyl)-2-thienyl]acetyl]amino]-8-oxo-5-thia-1-azabicyclo]4.2.0.]-oct-2-ene-2-carboxylic acid A mixture of 1.2 equivalents of 5-chloromethyl-2-thienylacetyl chloride and 1 equivalent of 7-aminocephalosporanic acid is refluxed for 50 minutes in ethyl acetate after which the solvent is removed and the remaining product is purified by column chromatography on silica gel to give 3-[(acetyloxy)methyl]-7-[[2-[5-(chloromethyl)-2-thienyl]acetyl]amino]-8-oxo-5-thia-1-azabicyclo[4.2.0.]oct-2-ene-2-carboxylic acid.

EXAMPLE 15 p-Chloromethylphenylglycine

When in the procedure of Example 1 A acetylated phenylglycine is substituted for phenylacetic acid with the additional step of acid hydrolysis to remove the amine protecting group, p-chloromethylphenylglycine is obtained.

EXAMPLE 16

3-[(Acetyloxy)methyl]-7-[[2-[4-(chloromethyl)-phenyl]-2-aminoacetyl]amino]-8-oxo-5-thia-1-azabicyclo[4.2.0.]oct-2-ene-2-carboxylic acid p-Chloromethylphenylglycine wherein the amino group is protected with tert-butoxycarbonyl, is treated with isobutyl chloroformate in the presence of trithylamine. The thus obtained mixed anhydride is reacted with 7-aminocephalosporanic acid triethylamine salt at 0°C for about 4 hours. The resulting product is isolated, and the amino protecting group is removed by acid hydrolysis to give, 3-[(acetyloxy)methyl-7-[[2-[4-(chloromethyl)phenyl]-2-aminoacetyl]-amino]-8-oxo-5-thia-1-azabicyclo[4.2.0]-oct-2-ene-2-carboxylic acid.

EXAMPLE 17

When in the procedure of Example 1 A equivalent amounts of the following acids are substituted for phenylacetic acid the corresponding chloromethylated derivative is obtained:

| Acid | Chloromethylated Derivative |
| --- | --- |
| α-hydroxy-2-thienyl-acetic acid | α-hydroxy-5-chloromethyl-2-thienylacetic acid |
| o-chlorophenyl-acetic acid | o-chloro-p-chloromethyl-phenylacetic acid |

EXAMLE 18

When in the procedure of Example 1 B an equivalent amount of α-hydroxy-5-chloromethyl-2-thienylacetic acid or o-chloro-p-chloromthylphenylacetic acid is substituted for p-chloromethylphenylacetic acid the following compounds are obtained:
α-hydroxy-5-chloromethyl-2-thienylacetyl chloride, o-chloro-p-chloromethylphenylacetyl chloride.

EXAMPLE 19

When in the procedure of Example 2,, an equivalent amount of α-hydroxy-5-chloromethyl-2-thienylacetyl chloride or o-chloro-p-chloromethylphenylacetyl chloride is substituted for p-chloromethylphenylacetyl chloride, the follwoing products are obtained:
3-[(acetyloxy)methyl]-7-[[2-[5-chloromethyl)2-thienyl]2-hydroxyacetyl]amino]-8-oxo-5-thia-1-azabicyclo[4.2.0.]-oct-2-ene-2-carboxylic acid, 3-[(acetyloxy)methyl]7-[[2-[2-chloro-5-chloromethyl)-phenyl]acetyl]amino]-8-oxo-5-thia-1-azabicyclo[4.2.0.]-oct-2-ene-2-carboxylic acid.

EXAMPLE 20

When in the procedure of Example 11 A an equivalent amount of one of the acids listed below is substituted for phenoxyacetic acid, the corresponding chloromethylated derivative listed below is obtained:

| Acid | Chloromethylated Derivative |
|---|---|
| p-isopropylphenoxyacetic acid | o-chloromethyl-p-isopropylphenoxyacetic acid |
| o-methyl-α-methylphenoxyacetic acid | p-chloromethyl-o-methylphenoxyacetic acid |
| o-chlorophenylthioacetic acid | p-chloromethyl-o-chlorophenylthioacetic acid |
| α-methylphenylthioacetic acid | p-chloromethyl-α-methylphenylthioacetic acid |

EXAMPLE 21

When in the procedure of Example 11 B o-chloromethyl-p-isopropylphenoxyacetic acid, p-chloromethyl-o-methyl-o-methylphenoxyacetic acid, p-chloromethyl-o-chlorothioacetic acid or p-chloromethyl-α-methylphenylacetic acid is substituted for 2,4-bis(chloromethyl)phenoxyacetic acid, the corresponding acid chloride is obtained.

EXAMPLE 22

When in the procedure of Example 12, an equivalent amount of each of the acid chloride compounds obtained in Example 21 is substituted for 2,4-bis(chloromethyl)-pheoxyacetyl chloride, the following products are obtained: 3-[(acetyloxy)methyl]-7-[[2-[2-chloromethyl-4-isopropylphenoxy]acetyl]amino]-8-oxo-5-thia-1-azabicyclo[4.2.0.]-oct-2-ene-2-carboxylic acid, 3-[(acetyloxy)methyl]-7-[[2-[4-chloromethyl-2-methylphenoxy]acetyl]amino]-8-oxo-5-thia-1-azabicyclo[4.2.0.]oct-2-ene-2-carboxylic acid, 3-[(acetyloxy)methyl]-7-[[2-[2-chloro-4-chloromethylphenoxy]acetyl]amino]-8-oxo-5-thia-1-azabicyclo]4.2.0.]oct-2-ene-2-carboxylic acid, 3-[(acetyloxy)methyl]-7-[[2-[4-chloromethylphenoxy]acetyl]-amino]-8-oxo-5-thia-1-azabicyclo[4.2.0-.]oct-2-ene-2-carboxylic acid.

EXAMPLE 23

When in the procedure of Example 1A, an equivalent amount of phenylmalonic acid diethyl ester of α-carboxy-2-thienylacetic acid diethyl ester is substituted for phenylacetic acid, p-chloromethylphenylmolonic acid diethyl ester and 4- and 5-chloromethyl-α-carboxy-2-thienylacetic acid diethyl ester are obtained. Acid hydrolysis of the products yields the corresponding acids.

EXAMPLE 24

3-[(Acetyloxy)methyl]-7-[[2-[4-(chloromethyl)-phenyl]-2-carboxyacetyl]amino]-8-oxo-5-thia-1-azabicyclo[4.2.0.]-oct-2-ene-2-carboxylic acid 4 g of thienyl acetyl nitrophenyl polymer, prepared according to the procedure described in Canadian Pat. No. 895,580, with 1 m. mole per gram of p-chloromethylphenylmalonic acid are suspended for about 8 hours in 20 ml of dry methylene chloride solution containing 1 m. mole of 7-aminocephalosporanic acid triethylammonium salt, which is prepared from 544 mg of 7-aminocephalosporanic acid (1m. mole) and 0.56 ml of triethylamine (1 m. mole) at room temperature. After only traces of 7-aminocephalosporanic acid remain in solution, which is determined by thin layer chromotography on cellulose in 70% aqueous propanol, the polymer is filtered off and washed with 3 portions of 50 ml each of methylene chloride. The combined filtrates are evaporated and the residue is dissolved in 20 ml of distilled water. This solution is acidified to pH 2 by adding 0.2N hydrochloric acid and extracted twice with ethyl acetate. The solution is dried over sodium sulfate and evaporated at room temperature. The remaining solid is dried overnight over phosphorus pentoxide under vacuum to give 3-[(acetyloxy)methyl]-7-[[2-[4-(chloromethyl)-phenyl]-2-carboxyacetyl]amino]-8-oxo-5-thia-1-azabicyclo-[4.2.0.]-oct-2-ene-2-carboxylic acid.

EXAMPLE 25

3-[(Acetyloxy)methyl]-7-[[2-[5-(chloromethyl)-2-thienyl]-2-carboxyacetyl]amino]-8-oxo-5-thia-1-azabicyclo[4.2.0.]-oct-2-ene-2-carboxylic acid When in the procedure of Example 24, an equivalent amount of 5-chloromethyl-α-carboxy-2-thienylacetic acid is substituted for p-chloromethylphenylmalonic acid, 3-[(acetyloxy)methyl]-7-[[2-[5-(chloromethyl)-2-thienyl]-2-carboxyacetyl]amino]-8-oxo-5-thia-1-azabicyclo[4.2.0.]oct-2-ene-2-carboxylic acid is obtained.

We claim:
1. A compound of the formula

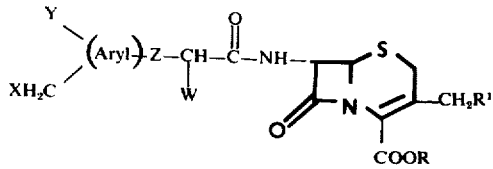

wherein Aryl is selected from phenyl or 2-thienyl; X is selected from chlorine, bromine or fluorine; Y is selected from hydrogen, chlorine, bromine, straight or branched lower alkyl of from 1 to 4 carbon atoms, lower alkoxy of from 1 to 4 carbon atoms, or —CH$_2$X wherein X is selected from bromine, chlorine or fluorine, with the proviso that when Aryl represents 2-thienyl, Y is hydrogen; Z is selected from a bond, oxygen or sulfur with the proviso that when Aryl is 2-thienyl, Z is a bond; W is selected from hydrogen, methyl, hydroxy, amino, —COOH, or —SO$_3$H with the proviso that when Z is oxygen or sulfur, W is other than hydroxy; R is selected from hydrogen or a pharmaceutically acceptable non-toxic cation; and R$^1$ is selected from hydrogen or acetoxy.

2. A compound of claim 1 wherein Aryl is 2-thienyl.
3. A compund of claim 2 wherein W is selected from hydrogen or methyl.
4. A compound of claim 3 wherein Z is a bond.
5. A compound of claim 1 wherein Aryl is phenyl.
6. A compound of claim 5 wherein W is selected from hydrogen, methyl, amino or hydroxy.
7. A compound of claim 6 wherein Z is a bond.
8. A compound of claim 7 wherein Y is selected from hydrogen or lower alkoxy.
9. A compound of claim 8 which is 3-[(acetyloxy)-methyl]-7-[[2-[4-(chloromethyl)phenyl]acetyl- ]amino]-8-oxo-5-thia-1-azabicyclo[4.2.0]oct-2-ene-2-carboxylic acid or a pharmaceutically acceptable salt thereof.

10. A compound of claim 8 which is 7-[[2-[4-(chloromethyl)phenyl]acetyl]amino]-3-methyl-8-oxo-5-thia-1-azabicyclo[4.2.0.]oct-2-ene-2-carboxylic acid or a pharmaceutically acceptable salt thereof.

11. A compound of claim 8 which is 7-[[2-[2-bromomethyl)phenyl]acetyl]amino]-3-methyl-8-oxo-5-thia-1-azabicyclo[4.2.0]oct-2-ene-2-carboxylic acid or a pharmaceutically acceptable salt thereof.

12. A compound of claim 8 which is 3-[(acetyloxy)methyl]-7-[[2-[2-(chloromethyl)-4-methoxyphenyl]-2-hydroxyacetyl]amino]-8-oxo-5-thia-1-azabicyclo[4.2.0]oct-2-ene-2-carboxylic acid or a pharmaceutically acceptable salt thereof.

13. A compound of claim 8 which is 7-[[2-[2-(chloromethyl)-4-methoxyphenyl]-2-hydroxyacetyl]amino]-3-methyl-8-oxo-5-thia-1-azabicyclo[4.2.0]oct-2-ene-2-carboxylic acid or a pharmcaeutically acceptable salt thereof.

14. A compound of claim 6 wherein Z is oxygen or sulfur.

15. A compound of claim 14 wherein Y is selected from hydrogen or lower alkoxy.

16. A compound of claim 1 which is 3-[(acetyloxy)methyl-7-[[2-[2,4-bis(chloromethyl)phenyl]acetyl]amino]-8-oxo-5-thia-1-azabicyclo[4.2.0]oct-2-ene-2-carboxylic acid or a pharmaceutically acceptable salt thereof.

17. A compound of claim 15 which is 3-[(acetyloxy)methyl]-7-[[2-[2,4-bis(chloromethyl)phenoxy]acetyl]amino]-8-oxo-5-thia-1-azabicyclo[4.2.0]oct-2-ene-2-carboxylic acid or a pharmaceutically acceptable salt thereof.

* * * * *